United States Patent [19]

Wurtman et al.

[11] Patent Number: 4,649,161

[45] Date of Patent: Mar. 10, 1987

[54] METHOD FOR TREATING DEPRESSION WITH D-FENFLURAMINE

[75] Inventors: Richard J. Wurtman; Judith J. Wurtman, both of Boston; Dermot O'Rourke, Charlestown, all of Mass.

[73] Assignee: Massachusetts Institute of Technology, Cambridge, Mass.

[21] Appl. No.: 874,609

[22] Filed: Jun. 16, 1986

[51] Int. Cl.⁴ .............................................. A61K 31/135
[52] U.S. Cl. ..................................................... 514/654
[58] Field of Search ......................................... 514/654

[56] References Cited

U.S. PATENT DOCUMENTS 4,309,445  1/1982  Wurtman et al. ................... 514/654
4,452,815  6/1984  Wurtman et al. ................... 514/654

Primary Examiner—Stanley J. Friedman
Attorney, Agent, or Firm—Paul J. Cook

[57] ABSTRACT

D-fenfluramine is administered to a human patient having seasonal depression or other forms of bipolar depression in order to alleviate or cure the depression.

2 Claims, No Drawings

METHOD FOR TREATING DEPRESSION WITH D-FENFLURAMINE

BACKGROUND OF THE INVENTION

This invention relates to a method for treating depression in humans with d-fenfluramine.

Bipolar depressions often, but not always, are characterized by alternating periods of depression and hypomania. At the present time, there are available a wide variety of modes of treating patients afflicted with bipolar depression including psychiatric treatment and the administration of pharmaceutical compositions to the patient.

Prior to the present invention, the efficacy of d-fenfluramine in treating depression is specifically contraindicated, Physician's Desk Reference, 1985, page 1658. The d-fenfluramine has been disclosed in U.S. Pat. No. 3,198,834 to have an anorexigenic effect. In addition, U.S. Pat. No. 4,309,445 discloses that d-fenfluramine can be administered to patients having a syndrome of abnormal carbohydrate craving between meals in order to reduce the craving of carbohydrate without inhibiting the intake of protein by the patient.

SUMMARY OF THE INVENTION

The present invention is based upon the discovery that d-fenfluramine, when administered to a patient afflicted with a bipolar depression, effects a significant reduction in depression. This effect has been observed without observation of undesirable side effects.

DESCRIPTION OF SPECIFIC EMBODIMENTS

Bipolar depressions are included among the "Atypical Bipolar Disorder " [269.70] classification in DSM III and also include variants such as the "Seasonal Affective Disorder Syndrome" [SADS] not specifically listed in DSM-III. The depressive phase of the illness may be characterized by the following signs and symptoms: dysphoric mood or anhedonia; loss of interest in previously enjoyed activities or pastimes; hypersomnia; decreased energy, inability to concentrate, inability to think clearly; increased fatiguability; increased appetite, often both for calories and, specifically for carbohydrates; weight gain; psychomotor retardation; social withdrawal; decreased involvement and interest in work; the tendency to use drugs and/or alcoholic beverages and/or niccotine excessively to improve the mood; and suicidal tendencies. The hypomanic phase is characterized by heightened mood, a decreased need for sleep, increased energy, inflated self-esteem, increased productivity at work, sharpened and more creative thinking, an increase in socialization or gregariousness, and, often, a decrease in appetite, sometimes with light weight loss. One particular subset of such patients suffer from "SADS", exhibiting a tendency to become depressed each fall or winter and to stop being depressed with increased daylight. Another subset presents to their physcians primarily with symptoms related to appetite disturbances, e.g. carbohydrate craving leading to obesity; bulemia; anorexia nervosa with depression.

The present invention provides a method for treating bipolar depressive patients with a pharmaceutical composition having as an active ingredient the d-fenfluramine or 1-meta-trifluoro-methylphenyl-2-ethyl-amino-propane or a salt thereof mixed with an inert non-toxic pharmaceutical carrier.

Suitable additional salts can be formed from the following acids: the hydrohalic acid, sulfuric acid, phosphoric acid or an organic acid such as acetic acid, valeric acid, caprioc acid, benzoic or nicotinic acid.

The inert non-toxic pharmaceutical excipient of choice utilized depends on the mode of administration. The compositions of this invention are suitable for parenteral, buccal, sublingual or rectal administration. The resulting pharmaceutical compositions are, for example, tablets, coated tablets, capsules, soft gelatine capsules, drinkable emulsions, suspensions or solutions for oral or injectable administration, sublingual tablets or suppositories. They may also be formulated into a sustained release form. Among the various excipients which may be used for these purposes include talc, magnesium stearate, calcium carbonate, sodium or magnesium phosphate, lactose or silica or the like. To the solid forms may be added a filler, a diluent, a binder such as ethyl-cellulose, dihydroxypropyl cellulose, carboxymethylcellulose, arabic gum, tragacanth gum or gelatine. The compositions of this invention may also be flavored, colored or coated with a wax or a plasticizer.

For the bipolar depressive patient, the administration of a composition containing between about 2.5 to 60 mg of d-fenfluramine given once or twice a day daily, i.e., a total of 2.5-120 mg depending upon the body weight of the patient, decreases the depressive state of the patient. Most commonly, d-fenfluramine is administered in an amount of between about 5, 10 and 20 mg once or twice a day.

The following example illustrates the present invention and is not intended to limit the same.

EXAMPLE I

Eight patients (three males and five females, ages 28 to 52) were admitted for study to the Massachusetts Institute of Technology Clinical Research Center. The study was approved by the Massachusetts Institute of Technology Committee on Use of Humans as Subjects, protocol #1589; and the CRC Advisory Committee, protocol #237, and the US FDA, (IND 20.205, c5614-4 USA). Prior to treatment, subjects were screened to determine their eligibility, i.e., whether they met diagnostic criteria for bipolar depression. Baseline measurements were made of calorie and nutrient choices, mood and activity during the fall and spring. Subsequently during the winter months, the effect of d-fenfluramine on various depressive symptoms (including patterns of food intake and weight) were evaluated. Subjects received 15 mg of d-fenfluramine twice a day or its placebo for three weeks in a double-blind, cross-over design.

The severity of the depression was rated at the beginning and end of each treatment period utilizing a clinical interview by a psychiatrist and various depression rating scales. Psychomotor function was evaluated by use of a wrist activity monitor and calorie and nutrient intakes measured by allowing patients free access to a variety of isocaloric meal and snack choices.

Results

Five of the eight subjects showed a significant clinical improvement with a reduction in depression as evident on clinical examination and psychometric depression ratings; two additional subjects showed significant improvement in appetitive or depressive symptoms.

| Combined Hamilton and Addendum Scores | | | |
|---|---|---|---|
| Placebo initial | Placebo Final | Fenf. Inj. | Fen. Final |
| 24.5 ± 2.13 | 18.25 ± 3.96 | 22.4 ± 2.64 | 8.75 ± 2.27 |

Data are expressed as means and SEM

Data are expressed as means and SEM

The hyperphagia and excessive carbohydrate intake associated with the depression was significantly reduced in response to treatment with d-fenfluramine.

|  | Placebo initial | Placebo Final | Fenf. Inj. | Fen. Final |
|---|---|---|---|---|
| Calories | 3015 ± 559 | 2630 ± 284 | 2850 ± 493 | 1704 ± 340 |
| CHO/g | 280 ± 58 | 228 ± 33 | 260 ± 40 | 157 ± 39 |

Data are expressed as means and SEM

The following is an example of a typical response to treatment: A 30 year old single, white female who described a pattern (of approximately 10 years' duration) of sad and depressed mood, frequent crying, increased appetite, carbohydrate craving, hypersomnia, decreased energy, increased fatigue, inability to concentrate, lowered interest and social withdrawal and psychmotor retardation. These symptoms had their onset in September and terminated in April or May. With the advent of spring, she noted a distinct improvement in mood, accompanied by decreased sleep, increased energy, lowered calorie and carbohydrate intake and weight loss. Following treatment with d-fenfluramine, the subject was no longer depressed. She did not respond to placebo.

The treatment of the eight patients with d-fenfluramine caused an unequivocal amelioration of their depression in five (as measured by clinical criteria, the Hamilton Depression Rating Scale, and a "SAD" Depression Rating Scale addendum) and significant improvement of the depressive and/or appetitive symptoms in two.

We claim:

1. A method for treating human patients having bipolar depression which consists of administering to said patient a unit dosage from of a composition which comprises between about 2.5 mg and 120 mg per day of the dextro optically active isomer of 1-(meta-trifluoromethylphenyl)-2-ethylaminopropane or a physiologically acceptable salt thereof in admixture with an inert nontoxic carrier.

2. A method of claim 1 wherein the dosage of the active isomer ranges from 10 to 40 mg per day.

* * * * *